United States Patent
Lim et al.

(10) Patent No.: US 11,313,845 B2
(45) Date of Patent: Apr. 26, 2022

(54) HYDROGEN-DETECTING COMPOSITE PARTICLES AND MANUFACTURING METHOD THEREOF

(71) Applicant: DAEGU GYEONGBUK INSTITUTE OF SCIENCE AND TECHNOLOGY, Daegu (KR)

(72) Inventors: Sang Kyoo Lim, Daegu (KR); Seong Ho Hwang, Gyeonggi-do (KR); Young Kwang Kim, Daegu (KR)

(73) Assignee: DAEGU GYEONGBUK INSTITUTE OF SCIENCE AND TECHNOLOGY, Daegu (KR)

(*) Notice: Subject to any disclaimer, the term of this patent is extended or adjusted under 35 U.S.C. 154(b) by 87 days.

(21) Appl. No.: 16/499,778

(22) PCT Filed: Dec. 18, 2018

(86) PCT No.: PCT/KR2018/016091
§ 371 (c)(1),
(2) Date: Sep. 30, 2019

(87) PCT Pub. No.: WO2019/164113
PCT Pub. Date: Aug. 29, 2019

(65) Prior Publication Data
US 2020/0103385 A1    Apr. 2, 2020

(30) Foreign Application Priority Data
Feb. 21, 2018  (KR) .................. 10-2018-0020684

(51) Int. Cl.
| | |
|---|---|
| *G01N 33/00* | (2006.01) |
| *C01G 9/02* | (2006.01) |
| *G01N 31/22* | (2006.01) |
| *G01N 21/78* | (2006.01) |
| *C09C 3/06* | (2006.01) |
| *G01N 21/77* | (2006.01) |

(52) U.S. Cl.
CPC .............. *G01N 33/005* (2013.01); *C01G 9/02* (2013.01); *C09C 3/063* (2013.01); *G01N 21/783* (2013.01);
(Continued)

(58) Field of Classification Search
CPC ..... C01G 9/02; C01G 55/004; C01P 2004/64; C01P 2004/82; C09C 1/0081;
(Continued)

(56) References Cited

U.S. PATENT DOCUMENTS

| | | |
|---|---|---|
| 2004/0037740 A1 | 2/2004 | Liu et al. |
| 2017/0059538 A1* | 3/2017 | Noh ................ B01J 23/44 |

FOREIGN PATENT DOCUMENTS

| | | |
|---|---|---|
| KR | 20140134174 A | 11/2014 |
| KR | 101716966 B1 | 3/2017 |

(Continued)

OTHER PUBLICATIONS

Mohajeri et al, TEM-XRD analysis of PdO particles on TiO2 support for chemochromic detection of hydrogen, 2010, Sensors and Actuators, vol. 144, Issue 1, pp. 208-214 (Year: 2010).*
(Continued)

*Primary Examiner* — Benjamin R Whatley
*Assistant Examiner* — Austin Q Le
(74) *Attorney, Agent, or Firm* — Lex IP Meister, PLLC

(57) ABSTRACT

The present invention relates to hydrogen-detectable composite particles through irreversible discoloration and a method for manufacturing same. More particularly, the present invention relates to composite particles having palladium oxide (PdO) particles adhered on the surfaces of zinc oxide (ZnO) nanoparticles and a method for manufacturing same. In addition, the present invention relates to applications of hydrogen detecting sensors, nanofibers, polymer films, paints, or the like using the composite particles.

8 Claims, 1 Drawing Sheet

(52) U.S. Cl.
CPC ........ *G01N 31/224* (2013.01); *C01P 2004/03* (2013.01); *C01P 2004/04* (2013.01); *C01P 2004/64* (2013.01); *C01P 2004/82* (2013.01); *G01N 2021/7773* (2013.01)

(58) Field of Classification Search
CPC ........ C09C 1/043; C09C 3/063; G01N 21/78; G01N 21/783; G01N 31/224; G01N 33/005; G01N 2021/7773
See application file for complete search history.

(56) References Cited

FOREIGN PATENT DOCUMENTS

| KR | 101745128 B1 | 6/2017 | | |
|----|---|---|---|---|
| KR | 101872979 B1 | 7/2018 | | |
| WO | WO-2018152398 A1 | * | 8/2018 | ........... G01N 31/223 |

OTHER PUBLICATIONS

Karthikeyan L. et al., "Reliable, Room Temperature and Flow IndependentUV DrivenHydrogen Sensor", International Journal of Engineering Technology Science and Research, IJETSR, Jun. 2017, ISSN 2394-3386, pp. 585-591. vol. 4., Issue 6.

Karthikeyan L. et al., "Reliable and Flow Independent Hydrogen Sensor Based on Microwave-Assisted ZnO Nanospheres: Improved Sensing Performance Under UV Light at Room Temperature", IEEE Sensors Journal., vol. 18, No. 5, Mar. 1, 2018, pp. 1810-1819.

International Search Report (ISR) for International Application No. PCT/KR2018/016091, dated Mar. 19, 2019, with English Translation.

* cited by examiner (a) Preparation Example 1  (b) Comparative Preparation Example 1  (c) Comparative Preparation Example 2

(a) Preparation Example 1  (b) Comparative Preparation Example 1  (c) Comparative Preparation Example 2

HYDROGEN-DETECTING COMPOSITE PARTICLES AND MANUFACTURING METHOD THEREOF

CROSS-REFERENCE TO RELATED APPLICATIONS

This application is a U.S. National Stage of International Application No.: PCT/KR2018/016091 filed Dec. 18, 2018, and claiming the benefit of Korean Patent Application No.: 10-2018-0020684, filed Feb. 21, 2018, the entire contents of which are herein incorporated by reference.

TECHNICAL FIELD

The present invention relates to composite particles capable of sensing hydrogen by irreversible discoloration, and a method for preparing the same, and more particularly, to composite particles in which palladium oxide (PdO) particles are adhered on the surface of zinc oxide (ZnO) nanoparticles, and a method for preparing the same. The present invention also relates to applications of hydrogen-sensing sensors, nanofibers, polymer films, and coatings or the like utilizing the composite particles.

BACKGROUND ART

Hydrogen is a raw material used in ammonia synthesis, crude oil refining, hydrochloric acid production, and various metal oxide reduction or the like throughout the industry. In addition, hydrogen has a high energy density and its post-combustion by-product does not cause environment pollution. Thus, hydrogen has been pointed as an excellent source of energy capable of replacing fossil fuels. However, hydrogen has an explosion lower limit concentration in air of 4 vol. % and is odorless, colorless, and tasteless. Thus, it is difficult to sense hydrogen, so there is a great risk that dangerous disaster may occur upon leakage of hydrogen.

It is therefore necessary to develop a hydrogen sensor capable of sensing hydrogen precisely and rapidly throughout the industry using hydrogen. Hydrogen sensors developed so far operate on the principle of utilizing catalysts, or sensing changes in heat, electricity, resistance, and work function. However, these commercial hydrogen sensors have a disadvantage in that their application range is limited because they require external power supply.

Therefore, there is a need to develop a material which operates on the principle in which the sensing of hydrogen does not require an external power supply upon leakage of hydrogen, and there is a need to record whether or not hydrogen leakage occurs when utilizing this material throughout the industry. Thus, it is necessary to develop a material that may simultaneously satisfy irreversible sensing of hydrogen.

Variable hydrogen discoloration sensors have been developed to solve these problems. For example, alloys such as $PdO/TiO_2$, $Pd/WO_3$, $Pd/MoO_3$, $Pd/WO_3$—$SiO_2$, and $MoO_3/PtPd/Pt$ have been developed. However, the above-mentioned alloys have disadvantages such as an excessively high production cost and a still insufficient sensitivity, and thus cannot be widely used in the industrial field and are not actually commercialized in large quantities.

In addition, Korean Patent Laid-Open Publication No. 10-2014-0134174 discloses a sensor having a zinc oxide nanorod on which palladium (Pd) nanoparticles are deposited on a substrate, but the reaction efficiency of the sensor is significantly deteriorated with time due to oxygen and moisture.

Therefore, there is a need for a technique for preparing a material for a hydrogen sensor having sensitivity and economical efficiency, and development of a hydrogen-sensing sensor utilizing such technique is urgently required. In addition, it is necessary to develop a new detection sensor which is inexpensive, has a simple process, is durable, and has improved sensitivity, without deteriorating the sensitivity and responsiveness of the sensor.

DISCLOSURE

Technical Problem

An object of the present invention is to provide palladium oxide-zinc oxide composite particles capable of sensing hydrogen by irreversible discoloration.

Another object of the present invention is to provide palladium oxide-zinc oxide composite particles having high sensitivity to hydrogen gas which may be visually sensed smoothly even at a low concentration upon leakage of hydrogen.

Another object of the present invention is to provide palladium oxide-zinc oxide composite particles which are excellent in response selectivity to hydrogen even when various kinds of gas components are mixed, and thus is not affected by other gases.

Another object of the present invention is to provide hydrogen-sensing sensors, polymer films, nanofibers, and coatings wherein they have a significantly increased sensitivity to hydrogen gas by using the hydrogen-sensing palladium oxide-zinc oxide composite particles, may visually sense hydrogen smoothly even at a low concentration, and have excellent response selectivity to hydrogen even when various kinds of gas components are mixed, and thus are not affected by other gases.

Technical Solution

In one general aspect, a method for preparing hydrogen-sensing composite particles includes:

a) dissolving a palladium precursor in an aqueous acid solution to prepare an aqueous palladium oxide precursor solution; and b) mixing the aqueous palladium oxide precursor solution with zinc oxide particles and reacting them to prepare hydrogen-sensing composite particles in which palladium oxide nanoparticles growing in surface contact with each other are adsorbed on a surface of the zinc oxide particles.

In another general aspect, there is provided hydrogen-sensing composite particles in which palladium oxide nanoparticles in surface contact with each other are adsorbed on a surface of zinc oxide particles.

In another general aspect, there is provided a hydrogen-sensing sensor comprising the hydrogen-sensing composite particles.

In another general aspect, there is provided a coating composition comprising the hydrogen-sensing composite particles.

In another general aspect, there is provided a hydrogen-sensing sensor comprising a coating film formed by applying the coating composition.

Advantageous Effects

In hydrogen-sensing composite particles according to the present invention, visible color changes before and after hydrogen exposure are evident at a low concentration of hydrogen gas exposure, unlike the prior art, and thus the hydrogen sensing or sensitivity is significantly excellent, the hydrogen gas-sensitive selectivity is excellent, the long-term stability is excellent, the process is simple, and the manufacturing cost may be lowered.

In addition, hydrogen discoloration composite particles of the present invention, polymer films, fibers, coatings, and a method for preparing the same may prepare various types of hydrogen discoloration sensors having excellent discoloration performance by a further simplified process, and at the same time, it is possible to increase price competitiveness.

BEST MODE

Figure 1:
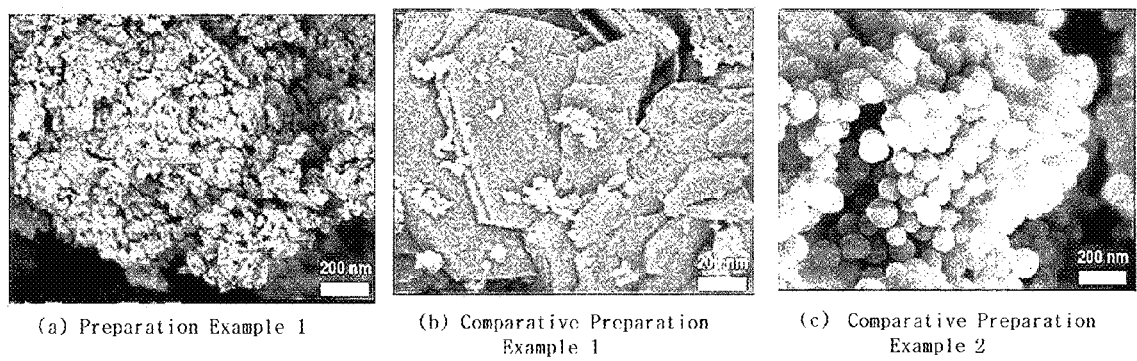
FIGS. 1A, 1B, and IC are SEM images of the composite particles of Preparation Example 1 and Comparative Preparation Examples 1 and 2 of the present invention, respectively.

Hereinafter, the present invention will be described in more detail with reference to embodiments and examples including accompanying drawings. The following specific examples and Examples are only a reference for describing the present invention in detail, and are not limited thereto, and may be implemented in various forms.

In addition, all technical terms and scientific terms have the same meanings as those commonly understood by a person skilled in the art to which the present invention pertains unless otherwise defined. The terms used herein are only for effectively describing certain embodiments, and not intended to limit the present invention.

In addition, singular forms used in the specification and the appended claims are intended to include the plural forms as well unless otherwise indicated in context.

The present invention may prepare hydrogen-sensitive composite particles having palladium oxide particles formed by adsorption onto the surface of zinc oxide particles, which is an object of the present invention as follows.

The inventors of the present invention have found an unusual phenomenon in which palladium oxide nanoparticles are very densely formed on the surface of zinc oxide particles when prepared by the following method, the unusual phenomenon being a unique phenomenon that may not be obtained from inorganic particles such as other metal oxides in the conventional art. Thus, the inventors of the present invention have found that even if hydrogen-sensing composite particles are prepared by the same process using metal oxides other than zinc oxide, in the case of using zinc oxide as compared with other kinds of particles, the concentration of palladium oxide adsorbed on the surface is adsorbed in a significantly large amount.

It was confirmed that in the hydrogen-sensing composite particles, visible color changes before and after hydrogen exposure are evident even at a low concentration of hydrogen gas exposure, unlike the prior art, and thus the hydrogen sensing or sensitivity is significantly excellent, the long-term stability is excellent, the process is simple, and the manufacturing cost may be lowered.

The scope of the present invention also includes that the composite particles of the present invention may be sufficiently mixed and stirred with a thermoplastic resin or a thermosetting resin, and injected or extruded to prepare a film, a tape, a sheet, or a three-dimensional molded body, or a conventional paint or a coating mixture may be prepared, applied, and dried, whereby the obtained object functions as a sensor capable of conducting early detection of hydrogen leakage due to fully irreversible discoloration even at a low concentration of hydrogen leakage.

An embodiment of the present invention is a method for preparing hydrogen-sensing composite particles including:

a) dissolving a palladium precursor in an aqueous acid solution to prepare an aqueous palladium oxide precursor solution; and b) mixing the aqueous palladium oxide precursor solution with zinc oxide particles and reacting them to prepare hydrogen-sensing composite particles in which palladium oxide nanoparticles growing in surface contact with each other are adsorbed on a surface of the zinc oxide particles.

An embodiment of the present invention may further include, after step b), c) separating and recovering the hydrogen-sensing composite particles, followed by drying at a temperature of 60 to 100° C.

In an embodiment of the present invention, in the hydrogen-sensing composite particles, the palladium oxide nanoparticles may be grown in surface contact with each other to be adsorbed on the surface of the zinc oxide particles.

In an embodiment of the present invention, the palladium oxide nanoparticles may have an average particle size of 0.1 to 30 nm.

In an embodiment of the present invention, the zinc oxide particles may have an average particle size of 10 to 1000 nm.

In an embodiment of the present invention, the aqueous acid solution may contain an inorganic or organic acid.

In an embodiment of the present invention, the aqueous acid solution may be an aqueous hydrogen chloride solution.

In an embodiment of the present invention, the palladium precursor and the aqueous acid solution may be mixed in a mixing ratio of 1:1.5 to 1:3 molar ratio.

In an embodiment of the present invention, a concentration of the aqueous palladium oxide precursor solution may be 0.05 to 10 mM.

In an embodiment of the present invention, a content of the zinc oxide particles may be 0.5 to 5 g/L.

In an embodiment of the present invention, in step b), the reaction may be stirred at 100 to 800 rpm for 1 to 60 minutes at a temperature of 10 to 90° C.

Another embodiment of the present invention is hydrogen-sensing composite particles in which palladium oxide nanoparticles in surface contact with each other are adsorbed on the surface of zinc oxide particles.

In an embodiment of the present invention, the hydrogen-sensing composite particles have a sea-island structure in which the zinc oxide particles are a sea portion, and the palladium oxide nanoparticles in surface contact with each other are an island portion.

In an embodiment of the present invention, the ratio of the surface area on which the palladium oxide nanoparticles in surface contact with each other are adsorbed, may be 50 to 100% of a surface area of the zinc oxide particles.

In an embodiment of the present invention, the zinc oxide particles may have an average particle size of 10 to 1000 nm.

In an embodiment of the present invention, the palladium oxide nanoparticles may have an average particle size of 0.1 to 30 nm.

In an embodiment of the present invention, a color difference ΔE represented by the following Equation 1 may be 20 or more, at 4 vol. % concentration of hydrogen:

$$\Delta E = [(L-L')^2 + (a-a')2 + (b-b')^2]^{1/2}$$ [Equation 1]

wherein ΔE is the color difference between samples, L is a brightness value measured under a condition of being exposed to 4 vol. % concentration of hydrogen for 2 minutes, L' is a brightness value measured before exposure to hydrogen, a is a position in a red-green axis measured under a condition of being exposed to 4 vol. % concentration of hydrogen for 2 minutes, a' is a position in the red-green axis measured before exposure to hydrogen, b is a position in a yellow-blue axis measured under a condition of being exposed to 4 vol. % concentration of hydrogen for 2 minutes, and b' is a position in the yellow-blue axis measured before exposure to hydrogen.

In an embodiment of the present invention, the hydrogen-sensing composite particles may exhibit irreversible color changes by hydrogen gas.

Another embodiment of the present invention is a hydrogen-sensing sensor comprising the hydrogen-sensing composite particles.

In an embodiment of the present invention, the hydrogen-sensing sensor may be any one form selected from the group consisting of a laminate, a film, a sheet, a fiber, and a three-dimensional molded body.

Another embodiment of the present invention is a coating composition comprising the hydrogen-sensing composite particles.

Another embodiment of the present invention is a hydrogen-sensing sensor comprising a coating film formed by applying the coating composition.

Hereinafter, each configuration of the present invention will be described in more detail.

First, a method for preparing hydrogen-sensing composite particles of the present invention will be described in more detail.

In the preparing method according to an embodiment of the present invention, step a) is a step of dissolving a palladium precursor in an aqueous acid solution to prepare an aqueous palladium oxide precursor solution.

More specifically, step a) is a step of stoichiometrically mixing the palladium precursor with an aqueous acid solution containing an inorganic or organic acid and reacting them to prepare an aqueous palladium oxide precursor solution.

More specifically, 0.05 to 10 mM concentration of a solution of hydrogenchloropalladate ($H_2PdCl_4$) may be prepared by mixing the palladium precursor in an aqueous hydrochloric acid solution at 1:1.5 to 1:3 molar ratio.

The palladium precursor may be used without limitation as long as it can be generally used as a precursor reagent containing palladium. Specific examples thereof include any one or a mixture of two or more thereof selected from palladium acetate, palladium chloride, and palladium nitrate. The palladium precursor may more preferably be palladium chloride.

The aqueous acid solution may be an inorganic or organic acid, and more specifically, for example, an aqueous hydrogen chloride solution, i.e., hydrochloric acid or the like, may be used as the inorganic acid. Acetic acid or the like may be used as the organic acid.

More specifically, the palladium precursor may be reacted stoichiometrically by mixing the palladium precursor with an aqueous hydrochloric acid solution at 1:1.5 to 1:3 molar ratio to prepare a solution of hydrogenchloropalladate ($H_2PdCl_4$).

In addition, the concentration of the aqueous palladium oxide precursor solution for growing the palladium oxide nanoparticles on the surface of the zinc oxide particles may be 0.05 to 10 mM, and the palladium precursor is dissociated into an aqueous solution containing 0.1 to 20 mM of hydrochloric acid to prepare hydrogenchloropalladate (palladium oxide precursor).

When the concentration of the palladium oxide precursor is less than 0.05 mM, palladium oxide may not grow well on the surface of the metal oxide particles. When the concentration of the palladium oxide precursor exceeds 10 mM, under such a condition, the metal oxide may be dissociated by excess HCl in the palladium precursor solution.

Next, step b) is a step of mixing the aqueous palladium oxide precursor solution with zinc oxide particles and reacting them to prepare hydrogen-sensing composite particles in which the palladium oxide nanoparticles growing in surface contact with each other are adsorbed on the surface of the zinc oxide particles.

The substrate of the composite particles of the present invention is zinc oxide (ZnO), and uniquely, when the zinc oxide was reacted with the palladium oxide precursor of the present invention, the amount of adsorbed in a nanoparticle form on the surface of the zinc oxide was significantly increased, rather than being formed as palladium oxide free particles or aggregates of themselves. The zinc oxide particles may have an average particle size of 10 to 1000 nm.

In the above step, the content of the zinc oxide is not particularly limited, but may be, for example, a concentration of 0.01 to 100 g/L, and preferably 0.1 to 5 g/L. In the above-mentioned range, when the aqueous palladium oxide precursor solution and zinc oxide particles are stirred at a high speed upon mixing them together to prepare composite particles by an acid-base reaction, most of the palladium oxide nanoparticles may be adsorbed on the surface of the zinc oxide particles, which is preferable. The composite particles prepared may have an average particle size of 10 to 1000 nm.

In an embodiment of the present invention, in the reaction step for preparing the hydrogen-sensing composite particles, the reaction is preferably sufficiently carried out at room temperature or 10 to 90° C. under sufficient stirring. More specifically, stirring may be carried out at a speed of 100 to 800 rpm, and preferably 400 to 600 rpm for 1 to 60 minutes, and preferably 1 to 30 minutes at a temperature of 10 to 90° C., and preferably 20 to 30° C. In the above-mentioned range, the hydrogen-sensing composite particles in which the palladium oxide is densely adsorbed on the surface of the zinc oxide particles may be prepared.

In addition, in another embodiment of step b), an aqueous suspension of zinc oxide nanoparticles is prepared, and the aqueous suspension of zinc oxide nanoparticles is reacted with the aqueous palladium precursor solution to adsorb palladium oxide on the surface of the zinc oxide particles.

Next, after step b), the step of separating and recovering the hydrogen-sensing composite particles, followed by drying may be further included. More specifically, it may be filtered to separate and recover the solid content, followed by drying. Here, the drying may be performed using hot air, an oven or the like, and may be performed at a temperature of 60 to 100° C., and more specifically 70 to 90° C.

The hydrogen-sensing composite particles of an embodiment of the present invention prepared according to the preparing method as described above are hydrogen-sensing composite particles in which the palladium oxide nanoparticles in surface contact with each other are adsorbed on the surface of zinc oxide particles.

The hydrogen-sensing composite particles may have a sea-island structure in which the zinc oxide particles are a sea portion, and the palladium oxide nanoparticles in surface contact with each other are the island portion. That is, the palladium oxide nanoparticles in surface contact with each other may be adsorbed on the surface of the zinc oxide particles, and the aggregate of the palladium oxide nanoparticles may form the island portion.

Here, a ratio of the surface area on which the palladium oxide nanoparticles in surface contact with each other are adsorbed, may be 50 to 100% of the surface area of the zinc oxide particles. That is, the area of the aggregates in which the palladium oxide nanoparticles in surface contact with each other are aggregated may be 50 to 100% of the surface area of the zinc oxide particles.

In an embodiment of the present invention, the average particle size of the palladium oxide nanoparticles grown on the surface of the zinc oxide may be 1 to 20 nm. When average particle size thereof exceeds 20 nm, the surface area is reduced, and thus the change in color may not be apparent.

In an embodiment of the present invention, the palladium oxide nanoparticles may be grown on the surface of the zinc oxide particles and adsorbed thereon at a weight ratio of the zinc oxide particles and the palladium oxide nanoparticles of 100:0.01 to 100:15. In the range of the above-mentioned content, the sensitivity performance is good, the sensing selectivity to hydrogen gas is more excellent, and it is economical, which is preferable.

In addition, in the hydrogen-sensing composite particles of the present invention, the palladium oxide nanoparticles grow on the surface of zinc oxide, while being in surface contact with each other, where the higher the contact ratio, the greater the hydrogen sensing capability. Although not particularly limited, as shown in FIG. 1A of the present invention, it is particularly preferable to grow the palladium oxide particles so that the area of the contacting palladium oxide particles is 50% or more, and more specifically 50 to 100% of the surface of the zinc oxide particles. More preferably, it is most preferable that the palladium oxide nanoparticles are surface contact with the entire surface of the zinc oxide particles so as to be connected to each other. The surface area may be easily determined by measuring using a photograph such as SEM, and thus it will not be described in detail here. For example, the surface area may be determined by adjusting the magnification so as to include four or more zinc oxide particles, measuring at least 10 areas in which the surface of the zinc oxide particles are visible without connecting the palladium oxide nanoparticles, and then averaging them.

In addition, the hydrogen-sensing composite particles of the present invention exhibit irreversible color changes by hydrogen gas, and the color difference ΔE represented by the following Equation 1 may be 20 or more, and more specifically 20 to 72, at 4 vol. % concentration of hydrogen:

$$\Delta E=[(L-L')^2+(a-a')2+(b-b')^2]^{1/2}$$ [Equation 1]

wherein ΔE is the color difference between samples, L is a brightness value measured under a condition of being exposed to 4 vol. % concentration of hydrogen for 2 minutes, L' is a brightness value measured before exposure to hydrogen, a is a position in a red-green axis measured under a condition of being exposed to 4 vol. % concentration of hydrogen for 2 minutes, a' is a position in the red-green axis measured before exposure to hydrogen, b is a position in a yellow-blue axis measured under a condition of being exposed to 4 vol. % concentration of hydrogen for 2 minutes, and b' is a position in the yellow-blue axis measured before exposure to hydrogen.

Another embodiment of the present invention is a hydrogen-sensing sensor comprising the hydrogen-sensing composite particles according to an embodiment of the present invention.

In an embodiment of the present invention, the hydrogen-sensing sensor is any one form selected from the group consisting of a laminate, a film, a sheet, a fiber, and a three-dimensional molded body.

In addition, the hydrogen-sensing sensor may include a coating film formed by applying a coating composition comprising the hydrogen-sensing composite particles according to an embodiment of the present invention.

Specifically, the scope of the present invention also includes that the hydrogen-sensing composite particles may be sufficiently mixed and stirred with a thermoplastic resin or a thermosetting resin, and injected or extruded to prepare a film, a tape, a sheet, or a three-dimensional molded body, or a conventional paint or a coating mixture may be prepared, applied, and dried, whereby the obtained object functions as a sensor capable of conducting early detection of hydrogen leakage due to fully irreversible discoloration even at a low concentration of hydrogen leakage.

In addition, the present invention may use three-dimensional molded body or any one body selected from the group consisting of paper, polymer film, ink, dye and paint containing the hydrogen-sensing composite particles, but is not limited thereto.

Specifically, the fiber, film, sheet, three-dimensional molded body or the like containing the hydrogen-sensing composite particles may be processed by conventional methods such as spinning, hollow molding, blow molding, injection molding, casting, and extrusion of the resin composition comprising the composite particles.

Specifically, the resin composition may include, for example, various thermoplastic resins or thermosetting resins such as various polyesters such as polyamide and polyethylene terephthalate; polysulfone; polyether; polyacrylate-based resins; polyimide-based resins; urethane-based resins; epoxy-based resins; polyolefin-based resins including polypropylene or polyethylene; polyvinyl alcohol-based resins; polyvinyl acetate-based resin; and polyketone-based resins, as a resin component.

In an embodiment of the present invention, when manufacturing the hydrogen-sensing sensor containing the hydrogen-sensing composite particles, the content of the hydrogen-sensing composite particles may be 0.01 to 70 parts by weight, more preferably 0.5 to 20 parts by weight, and still more preferably 0.5 to 10 parts by weight, based on a resin, paper, or other inorganic component, which is a matrix material. However, the content thereof may be varied and used depending on the application, and there is no need to limit the content thereof.

In an embodiment of the present invention, the content of the hydrogen-sensing composite nanoparticles according to an embodiment of the present invention in the hydrogen-sensing sensor may be, but is not limited thereto, 0.1 to 20 wt. %, and preferably 1 to 10 wt. %.

Further, the present invention may be used as a sensor by preparing a laminate prepared by coating a solution or suspension containing the hydrogen-sensing composite particles and a binder on a substrate.

In the present invention, the molded body or sensor comprising the composite nanoparticles comes into contact with hydrogen gas, it turns black, and even when the contact between the molded body or sensor and hydrogen is terminated, the color is irreversible and thus does not return to its original state. Thus, it is always possible to know the state of hydrogen leaking at any time, so unlike other sensors which are reversibly changed, safety may be more secured.

In addition, all embodiments of the present invention are characterized by being irreversible hydrogen-sensing composite particles, sensors, and devices that do not return to their original colors after they have reacted with hydrogen gas.

In the discoloration composite nanoparticles for hydrogen sensing, visible color changes before and after hydrogen exposure is distinct from conventional exposure to hydrogen gas at low concentrations, unlike the prior art, and thus the hydrogen sensing or sensitivity is significantly excellent, the hydrogen gas-sensitive selectivity is excellent, the long-term stability is excellent, the process is simple, and the manufacturing cost may be lowered.

Hereinafter, the present invention will be described in more detail based on examples and comparative examples. However, the following examples and comparative examples are an example for describing the present invention in more detail, and the present invention is not limited by the following examples and comparative examples.

Preparation Example 1

Palladium oxide-zinc oxide composite particles in which palladium oxide is formed by growing on the surface, were prepared as follows.

Palladium chloride ($PdCl_2$) was dissolved in a hydrochloric acid (HCl) solution at a molar ratio of 1:2 to prepare a 0.1 mM hydrogenchloropalladate ($H_2PdCl_4$) solution. The zinc oxide nanoparticles (SUNZNO 150 nm, Sunjin Chem. Co., Ltd.) were added to the hydrogenchloropalladate solution at a concentration of 2 g/L, and then the mixture was evenly stirred at a speed of 500 rpm for 5 minutes at room temperature (25° C.). The composite particles in the stirred suspension were filtered using a 0.1 μm filter, and then dried in an oven at 80° C. to prepare palladium oxide-zinc oxide composite particles for hydrogen sensing.

Figure 2:
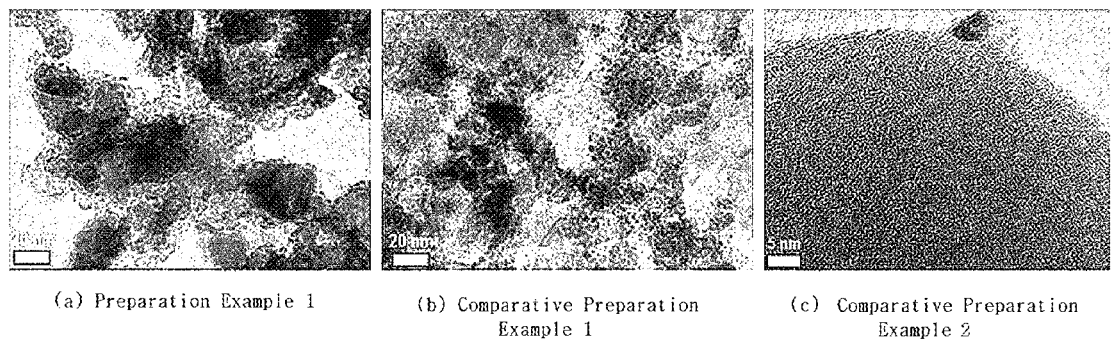
FIGS. 2A, 2B, and 2C are TEM images of Preparation Example 1 and Comparative Preparation Examples 1 and 2 of the present invention, respectively.

FIGS. 1A and 2A show scanning electron microscope (SEM) and transmission electron microscope (TEM) photographs showing the surface of the palladium oxide-zinc oxide composite particles prepared in Example 1, respectively. As the results of observation of FIGS. 1A and 2A, it was found that the palladium oxide-zinc oxide composite particles are a state in which zinc oxide having a size of 150 nm is aggregated, and the surface of zinc oxide is densely covered with the palladium oxide particles of about 2 nm in size.

It was also confirmed that from an X-ray diffraction pattern and an X-ray photoelectron spectrum of the palladium oxide-zinc oxide composite particles, the palladium oxide-zinc oxide composite nanoparticles were formed.

In addition, in order to investigate the degree of color conversion of the prepared composite particles to hydrogen gas, the palladium oxide-zinc oxide composite particles thus prepared were pressured in the form of circular pellets to prepare two, and then one was placed inside a hydrogen reactor with a volume of 80 ml. Subsequently, 4 vol. % concentration of hydrogen gas was blown onto the reactor at a rate of 50 ml/s for about 2 minutes, the absorption reflection spectrum of the pellet in contact with hydrogen and the pellet not in contact with hydrogen was measured through a spectroscope, and then the color difference was calculated by L, a, and b coordinate transformation. The results are recorded in Table 1 below.

Preparation Example 2

The process was performed in the same manner as Preparation Example 1, except that a 0.05 mM hydrogenchloropalladate solution was used. In addition, the color difference was measured in the same manner as in Preparation Example 1 and is recorded in Table 1.

Preparation Example 3

The process was performed in the same manner as Preparation Example 1, except that a 0.5 mM hydrogenchloropalladate solution was used. In addition, the color difference was measured in the same manner as in Preparation Example 1 and is recorded in Table 1.

Preparation Example 4

The process was performed in the same manner as Preparation Example 1, except that a 1 mM hydrogenchloropalladate solution was used. In addition, the color difference was measured in the same manner as in Preparation Example 1 and is recorded in Table 1.

Preparation Example 5

The process was performed in the same manner as Preparation Example 1, except that a 5 mM hydrogenchloropalladate solution was used. In addition, the color difference was measured in the same manner as in Preparation Example 1 and is recorded in Table 1.

Preparation Example 6

The process was performed in the same manner as Preparation Example 1, except that a 10 mM hydrogenchloropalladate solution was used. In addition, the color difference was measured in the same manner as in Preparation Example 1 and is recorded in Table 1.

Comparative Preparation Example 1

The process was performed in the same manner as Preparation Example 1, except that magnesium oxide was used instead of zinc oxide. FIGS. 1B and 2B are scanning electron microscope (SEM) and transmission electron microscope (TEM) photographs showing the surface of the palladium oxide-zinc oxide composite particles prepared in Example 1, respectively. As a result, it can be seen that from the scanning electron microscope (SEM) and transmission electron microscope (TEM) photographs showing the surface, the content of palladium oxide present on the surface of titanium dioxide was significantly smaller than that of the palladium oxide-zinc oxide composite particles prepared in Preparation Example 1.

Comparative Preparation Example 2

The process was performed in the same manner as Preparation Example 1, except that silicon dioxide (quartz) was used instead of zinc oxide. FIGS. 1C and 2C are the scanning electron microscope (SEM) and the transmission electron microscope (TEM) photographs showing the surface of the palladium oxide-zinc oxide composite particles prepared in Example 1, respectively. It was confirmed that from the scanning electron microscope (SEM) and transmission electron microscope (TEM) photographs, palladium oxide or palladium particles having a size of about 2 nm are present in a very small amount on the surface of the silicon dioxide. In addition, it was confirmed that as the result of the same color difference experiment as in Preparation Example 1, the composite particles had a very low color difference and thus the sensitivity to hydrogen gas was greatly reduced, as shown in Table 1 below.

TABLE 1

| | Metal oxides | $H_2PdCl_4$ concentration (mM) | Color difference ($\Delta E$) |
|---|---|---|---|
| Preparation Example 1 | ZnO | 0.1 | 28.72 |
| Preparation Example 2 | ZnO | 0.05 | 21.25 |
| Preparation Example 3 | ZnO | 0.5 | 45.21 |
| Preparation Example 4 | ZnO | 1 | 57.37 |
| Preparation Example 5 | ZnO | 5 | 63.28 |
| Preparation Example 6 | ZnO | 10 | 71.57 |
| Comparative Preparation Example 1 | MgO | 0.1 | 10.47 |
| Comparative Preparation Example 2 | $SiO_2$ | 0.1 | 1.70 |

In addition, to test the selectivity to hydrogen gas, Table 2 shows the results of color difference experiments in the atmosphere of 4 vol. % hydrogen and the remaining 96 vol. % nitrogen, 4 vol. % methane and the remaining 96 vol. % nitrogen, 4 vol. % carbon monoxide and the remaining 96 vol. % nitrogen. As shown in Table 2, it can be seen that the composite particles of the present invention shows the highest color difference with respect to hydrogen.

TABLE 2

| | 4 vol. % hydrogen/96 vol. % nitrogen | 4 vol. % methane/96 vol. % nitrogen | 4 vol. % carbon monoxide/96 vol. % nitrogen |
|---|---|---|---|
| Preparation Example 6 | 71.57 | 0.75 | 0.89 |

<Example 1> Preparation of Polyethylene Film Sensors

For a low-density polyethylene resin (LDPE, LG Chem) chip, the palladium oxide-zinc oxide composite particles prepared in Preparation Example 6 were extruded through an extruder at a discharge rate of 20 g/minute at 165° C., and pellets were prepared using a pelletizer. Subsequently, the pellets thus prepared were subjected to a hot press at 165° C. and a pressure of 60 bar for 1 minute to prepare a 100 μm thick of LDPE film containing 0, 1, 3, and wt. % of the palladium oxide-zinc oxide composite particles.

Figure 3:
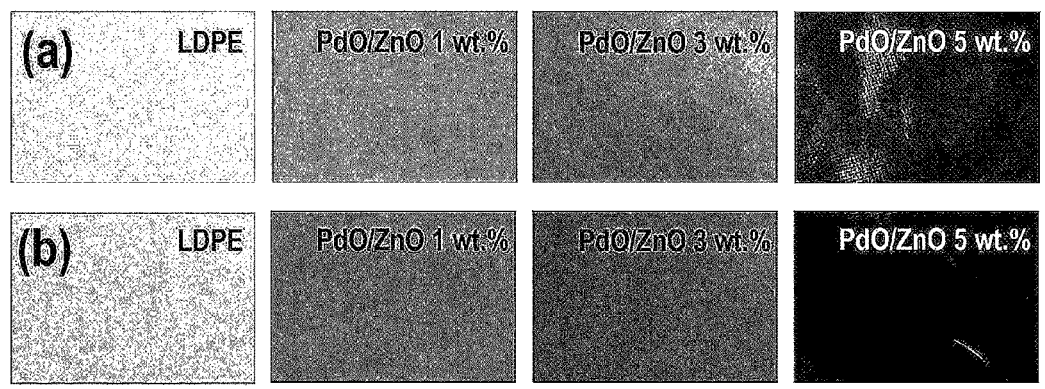
FIGS. 3A and 3B are photographs showing the film prepared according to Example 1, and photographs showing discoloration after the film is exposed to hydrogen, respectively.

FIG. 3A is photographs of the LDPE film containing 0, 1, 3, and 5 wt. % of the palladium oxide-zinc oxide composite particles prepared in Preparation Example 6, in order from left to right. FIG. 3B is photographs showing the results after exposure of 4 vol. % hydrogen gas for 5 minutes to the LDPE film containing 0, 1, 3, and 5 wt. % of the palladium oxide-zinc oxide composite particles prepared in Preparation Example 6, in order from left to right. It was confirmed that as the content of the palladium oxide-zinc oxide composite particles increases, the color of the original LDPE was changed from white to dark brown. In addition, it could be seen that in the case of the LDPE film containing 1 wt. %, 3 wt. %, and 5 wt. % of the palladium oxide-zinc oxide composite particles prepared in Preparation Example 6, the color difference after hydrogen exposure was 6.401, 7.441, and 8.978, respectively, indicating that the LDPE film containing 5 wt. % of the palladium oxide-zinc oxide composite particles had good performance for hydrogen sensing.

Example 2

A polyacrylonitrile solution was prepared by dissolving polyacrylonitrile (PAN) in N-dimethylformamide (DMF) solvent at 10 wt. %. To the polyacrylonitrile solution was added the palladium oxide-zinc oxide composite nanoparticles prepared in Preparation Example 6 to prepare a polyacrylonitrile dispersion containing the palladium oxide-zinc oxide composite nanoparticles.

The content of the palladium oxide-zinc oxide composite nanoparticles was 5 wt. % based on the weight of the polyacrylonitrile.

Meanwhile, the palladium oxide-zinc oxide composite nanoparticles were stirred for 24 hours or more so as to be well dispersed in the dispersion and mixed thoroughly. The polyacrylonitrile dispersion containing the palladium oxide-zinc oxide composite particles was subjected to electrospinning at an electric field of 20 kV to prepare composite fibers containing the palladium oxide-zinc oxide composite nanoparticles. It was confirmed that as the content of the palladium oxide-zinc oxide composite particles increases, the color of the original PAN nanofiber was changed from white to dark brown. When the nanofiber thus prepared was exposed to air containing 4 vol. % hydrogen for 2 minutes, the color difference was 14.7, indicating that the nanofiber had very good hydrogen sensitivity.

Example 3

A transparent acrylic-modified urethane solution was prepared by dissolving a water-based transparent acrylic-modified urethane (Jeongseok Chemical Corp.) in distilled water at 15 wt. %. A coating containing discolored palladium oxide-zinc oxide composite nanoparticles for hydrogen sensing was prepared by rapidly stirring the palladium oxide-zinc oxide composite particles prepared in Preparation Example 1 in the solution such that the mass ratio was 1:1. When the coating thus prepared was exposed to air containing 4 vol. % hydrogen for 2 minutes, the color difference was 16.3, indicating that the coatings had very good hydrogen sensitivity.

Hereinabove, although the present invention has been described by specific matters, exemplary embodiments, and drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-mentioned exemplary embodiments, but the claims and all of the modifications equal or equivalent to the claims are intended to fall within the scope and spirit of the present invention.

The invention claimed is:

1. Hydrogen-sensing composite particles comprising zinc oxide particles and palladium oxide nanoparticles disposed in surface contact with each other and adsorbed on a surface of the zinc oxide particles, wherein a color difference ΔE of the hydrogen-sensing composite particles is 40 or more, at 4 vol. % concentration of hydrogen, and the color difference ΔE is represented by the following Equation 1:

$$\Delta E=[(L-L')^2+(a-a')^2+(b-b')^2]^{1/2} \qquad \text{[Equation 1]}$$

wherein ΔE is the color difference between samples, L is a brightness value measured under a condition of being exposed to 4 vol. % concentration of hydrogen for 2 minutes, L' is a brightness value measured before exposure to hydrogen, a is a position in a red-green axis measured under a condition of being exposed to 4 vol. % concentration of hydrogen for 2 minutes, a' is a position in the red-green axis measured before exposure to hydrogen, b is a position in a yellow-blue axis measured under a condition of being exposed to 4 vol. % concentration of hydrogen for 2 minutes, and b' is a position in the yellow-blue axis measured before exposure to hydrogen.

2. The hydrogen-sensing composite particles of claim 1, wherein the hydrogen-sensing composite particles have a sea-island structure in which the zinc oxide particles are a sea portion, and the palladium oxide nanoparticles in surface contact with each other are an island portion.

3. The hydrogen-sensing composite particles of claim 1, wherein a ratio of the surface area on which the palladium oxide nanoparticles in surface contact with each other are adsorbed, is 50 to 100% of the surface area of the zinc oxide particles.

4. The hydrogen-sensing composite particles of claim 1, wherein the zinc oxide particles have an average particle size of 10 to 1000 nm.

5. The hydrogen-sensing composite particles of claim 1, wherein the palladium oxide nanoparticles have an average particle size of 0.1 to 30 nm.

6. The hydrogen-sensing composite particles of claim 1, wherein the hydrogen-sensing composite particles exhibit irreversible color changes by hydrogen gas.

7. A hydrogen-sensing sensor comprising a coating film formed by applying a coating composition comprising the hydrogen-sensing composite particles of claim 1.

8. The hydrogen-sensing sensor of claim 7, wherein the hydrogen-sensing sensor is any one form selected from the group consisting of a laminate, a film, a sheet, a fiber, and a three-dimensional molded body.

* * * * *